(12) United States Patent
Kahl

(10) Patent No.: US 8,001,857 B2
(45) Date of Patent: Aug. 23, 2011

(54) SAMPLE CHAMBER

(75) Inventor: Valentin Kahl, Martinsried (DE)

(73) Assignee: ibidi GmbH, Martinsried (DE)

( * ) Notice: Subject to any disclaimer, the term of this patent is extended or adjusted under 35 U.S.C. 154(b) by 409 days.

(21) Appl. No.: 12/143,678

(22) Filed: Jun. 20, 2008

(65) Prior Publication Data

US 2008/0314167 A1 Dec. 25, 2008

(30) Foreign Application Priority Data

Jun. 25, 2007 (EP) .................... 07012400

(51) Int. Cl.
*G01N 1/28* (2006.01)
*G01N 21/03* (2006.01)
*C12M 1/00* (2006.01)

(52) U.S. Cl. ............ 73/864.91; 422/547; 422/552; 422/559; 435/305.4; 356/246

(58) Field of Classification Search ........... 73/864.51, 73/864.91; 250/576; 356/246; 422/102, 422/939–940, 942–944, 547, 549, 550, 552, 422/559, FOR. 110; 435/305.1–305.4
See application file for complete search history.

(56) References Cited

U.S. PATENT DOCUMENTS

| | | | | |
|---|---|---|---|---|
| 4,562,725 A | * | 1/1986 | Oka et al. ................. 73/29.05 |
| 5,039,492 A | * | 8/1991 | Saaski et al. ............. 422/82.09 |
| 5,091,800 A | * | 2/1992 | Offenbacher et al. ........ 359/350 |
| 5,200,152 A | | 4/1993 | Brown |
| 5,229,282 A | * | 7/1993 | Yoshioka et al. ............ 435/177 |
| 5,460,777 A | * | 10/1995 | Kitajima et al. ............... 422/56 |
| 7,517,499 B2 | | 4/2009 | Kahl |
| 2002/0123671 A1 | * | 9/2002 | Haaland ........................ 600/300 |
| 2003/0044316 A1 | * | 3/2003 | Hirai et al. ..................... 422/56 |
| 2004/0131789 A1 | | 7/2004 | Brown |
| 2006/0246490 A1 | | 11/2006 | Anderson et al. |
| 2007/0009386 A1 | * | 1/2007 | Padmanabhan et al. ..... 422/68.1 |
| 2007/0017805 A1 | * | 1/2007 | Hodges et al. ............... 204/400 |
| 2007/0131549 A1 | * | 6/2007 | Cai et al. ................. 204/403.02 |
| 2009/0136982 A1 | * | 5/2009 | Tang et al. ..................... 435/29 |
| 2009/0253130 A1 | * | 10/2009 | Yoo ................................. 435/6 |
| 2010/0175488 A1 | * | 7/2010 | Kahl et al. ................. 73/864.91 |

FOREIGN PATENT DOCUMENTS

| | | |
|---|---|---|
| DE | 9203917 U1 | 5/1992 |
| DE | 10004135 A1 * | 8/2001 |
| DE | 10148210 A1 | 9/2003 |
| EP | 0437408 A2 | 7/1991 |
| EP | 1514596 A | 3/2005 |
| EP | 1750155 A | 2/2007 |
| WO | 03000416 A2 | 1/2003 |
| WO | 2004103890 A1 | 12/2004 |

\* cited by examiner

*Primary Examiner* — Thomas P Noland
(74) *Attorney, Agent, or Firm* — IP Strategies

(57) ABSTRACT

A sample chamber of plastics has at least one receiving area for receiving a liquid, and includes an oleophobic layer in a predetermined surface area. The sample chamber includes a base plate and a cover plate firmly connected thereto. The oleophobic layer is disposed on a side of the base plate and the cover plate facing away from the receiving areas, and/or the sample chamber consists of a plastic body and the oleophobic layer is disposed on a side of the plastic body facing away from the receiving areas.

27 Claims, 2 Drawing Sheets

SAMPLE CHAMBER

FIELD OF THE INVENTION

The invention relates to a sample chamber of plastics with a receiving area for receiving a liquid.

BACKGROUND OF THE INVENTION

Sample chambers of the aforementioned type are used, for example, to cultivate cell cultures or examine cells or molecules, in particular to observe them with a microscope. The sample chambers can be, for example, so-called 96-well plates, Petri dishes, tissue culture and/or cell culture flasks or object sample chambers.

A chamber for cell cultures is known, for example, from DE 100 04 135. A sample chamber in the form of a flow chamber is described in DE 101 48 210.

In the microscopy of molecules (for example DNA) or cells, the substances to be examined are placed in a receptacle or a reservoir of the sample chamber and can then be examined with high-resolution methods, such as by light-optical microscopy, fluorescence microscopy, confocal microscopy, etc.

It is a disadvantage of conventional sample chambers of plastics that these can be easily contaminated by liquids. For example, during the filling of a liquid reservoir or a liquid receptacle, a portion of the liquid can be placed next to the reservoir or exit from the same.

BRIEF SUMMARY OF THE INVENTION

In view of this disadvantage, it is the object of the invention to provide a sample chamber of plastics with at least one receiving area for receiving a liquid, which has a lower risk of contamination.

This object is achieved by a sample chamber according to claim 1.

According to the invention, a sample chamber of plastics with at least one receiving area for receiving a liquid is provided, wherein the sample chamber comprises a hydrophilic and/or an oleophobic layer in a predetermined surface area.

By means of such a layer it is achieved in particular that contaminating liquids cannot arbitrarily spread to or within the sample chamber. Here, the layer can be hydrophilic and/or oleophobic or lipophobic, respectively, in particular at room temperature (in the range of approx. 20° C. to 27° C., in particular 21° C. to 25° C.).

The layer can be in particular solvent-resistant, solvent-repellent and/or creeping agent-repellent. In this context, solvent-resistant means that the surface properties of the layer are not altered by a solvent; in particular, no solubilization or swelling takes place. Solvent-repellent or creeping agent-repellent means that the surface tension of the layer is lower than the surface tension of the solvent or the creeping agent. The solvents and creeping agents which are to be repelled by such layers or against which resistance is to be created can be present in a liquid as well as in a gaseous form.

In this manner, it is avoided that solvents or creeping agents employed in the manufacture or use of the sample chamber lead to a contamination or damage of the sample chamber. In particular, it is prevented that solvents or creeping agents form cracks or gaps in the sample chamber material or penetrate them.

The layer can have a surface tension of less than 25 mN/m, in particular less than 20 mN/m, in particular less than 15 mN/m, or of more than 70 mN/m, in particular more than 72 mN/m. In this manner, the preferably oleophobic or hydrophilic properties are in particular achieved.

The surface tension (or surface energy) is determined according to ISO 8296:2003 (plastics—films and sheetings—determination of the wetting tension, ISO 8296:2003). The ISO 8296 (former DIN 53 364) regulates the assessment of the medium wettability of plastics. The criterion is the behavior of the edge of strokes of a brush with test inks. Test inks with different surface tensions are used for this. If the edge of the stroke of the brush contracts within 2 seconds, the measurement is repeated with the next lower value. If the edge of the stroke of the brush runs outwards, the measurement is repeated with the next higher value. The (critical) surface energy is the value of the test liquid the edge of which stands still just for 2 seconds.

In a hydrophilic layer, it can be, for example, a $SiO_x$ layer. An oleophobic layer can be, for example, a silanisation or silane layer, a layer formed by a plasma treatment, in particular a low-pressure plasma treatment, or a corona treatment.

The layer can have a layer thickness of 1 nm to 50 μm, in particular of 50 nm to 10 μm. The layer can have an area of 1 $μm^2$ to 10 $cm^2$, in particular of 10 $μm^2$ to 10 $mm^2$.

In the sample chambers described above, the predetermined surface area can be arranged in a receiving area. Thereby, in particular the liquid distribution in the receiving area can be controlled. In a majority of receiving areas or reservoirs, the predetermined surface area can be provided in predetermined receiving areas, in particular in each receiving area.

The sample chambers described above can comprise at least two receiving areas, where the predetermined surface area is arranged between the at least two receiving areas. Thus, in particular in case of an oleophobic layer, cross-contamination between the two receiving areas can be prevented.

The sample chambers described above can comprise a base plate, where the base plate comprises at least one depression and/or at least one elevation by which a receiving area is formed. The base plate can for example comprise an elevation by which two receiving areas are separated from each other. The predetermined surface area can be arranged, for example, at this elevation, so that creeping of a liquid from one receiving area to the other one is prevented.

The depression in the base plate can comprise a base, so that by or with the cover plate, a hollow space is formed. Thus, the depression is not a through hole, but a blind hole. With such a hollow space in the sample chamber, examinations shielded from the surrounding area can be performed.

The depression in the base plate can have an oblong shape. For example, the depression can comprise a groove in the base plate. In this case, the receiving area is formed in the form of a channel and the sample chamber in the form of a flow chamber. Here, the predetermined surface area can be in particular provided in the region of the groove, in particular in the groove or in the area of the cover plate corresponding to the groove.

The base plate and/or the cover plate can comprise a channel coming from outside and ending in the receiving area, in particular a through hole. In particular, a through hole ending in the receiving area can be formed in the base plate. In the base plate, a groove for forming a channel can be provided. In particular, two or more channels ending in the receiving area can be provided.

Such a channel serves as inflow or outflow for the receiving area which can in this manner be filled with liquids and/or other substances.

The base plate can comprise a planar area and an elevation, a recess being formed in the elevation. The recess can also serve as receiving area and/or to receive an inflow means, such as a pipette. Furthermore, a one- or two-dimensional array of elevations (for example altogether 96 elevations) can be provided, a recess being formed in each elevation. In this case, the predetermined surface area can be arranged at each of these elevations. The predetermined surface area can thus comprise several partial areas which are spatially separated from one another.

The cover plate can have a thickness of 50 to 250 μm, preferably 100 to 200 μm. Such a cover plate advantageously permits the application of inverse microscopy.

The base plate and/or the cover plate can comprise plastics, in particular without double refraction and/or with an inherent fluorescence which is essentially equal to the fluorescence of a conventional cover glass. The conventional cover glass can be, for example, a pure white glass of hydrolytic Class 1, such as Menzel cover glass, in particular with a thickness of No. 1.5. Such a high-quality optical plastics improves microscopic examinations, in particular in the application of fluorescence microscopy. The cover plate can in particular comprise a flexible material, for example a film. The cover plate and the base plate can consist of the same material. The base plate and/or the cover plate can be embodied in the form of a molded body.

The base plate and/or the cover plate can be connected by means of adhesives, solvents, UV-treatment, radioactive treatment, laser treatment or thermal bonding. Thermal bonding can be effected sheet-like or strip-like, in particular only along the edge of the base plate and/or the cover plate. This advantageously permits a firm connection of base plate and cover plate.

Possible swelling agents to be used in solvent bonding are, for example, chloroform, acetone, toluene, benzene, heptane, ethanol, styrene, or mixtures thereof.

Possible plastics for the sample chambers, in particular for the base plate and/or the cover plate, are, for example, COC (cyclo-olefin-copolymer), COP (cyclo-olefin-polymer), PE (polyethylene), PS (polystyrene), PC (polycarbonate) or PMMA (polymethylmethacrylate).

The base area of the sample chamber can have the dimensions of a conventional microscope slide, in particular a width of 25.5 mm and a length of 75.5 mm, or of a multititer plate. The base area of the sample chamber can alternatively have a round shape, in particular with an outside diameter of for example 35 mm or 50 mm. A receiving area, in particular each receiving area, can have a volume of between 10 and 3000 μl, preferably of between 20 and 150 μl; the height can be between 5 μm and 10 mm, preferably between 0.1 mm and 0.5 mm, the width between 10 μm and 40 mm, preferably between 1 and 10 mm. The height of the sample chamber can be between 0.5 and 5 mm, preferably between 1 and 2 mm, in particular 1.7 mm, in a planar area of the base plate.

If the base plate of the sample chamber comprises an elevation in which a depression is formed, the volume of such a receiving means can be between 50 μl and 3 ml, preferably between 80 μl and 2.5 ml; the height of an elevation, starting from a planar area, can be between 1 mm and 1.5 cm, preferably between 5 mm and 1 cm. These receiving areas can in particular be a hollow space or channel formed by a groove in the base plate and a cover plate.

The layer can be formed all over one or several sides of the base plate and/or the cover plate. In particular in case of an oleophobic layer, oil-immersion objectives for high-resolution microscopy can be advantageously used. It is thus prevented that in inverse microscopy, the bottom of the sample chamber is wetted with oil and contaminated by it. It is furthermore prevented that the oil used creeps into the plastics of the sample chamber and causes tension cracks. Analogous results with respect to a prevention of creeping can be also achieved with a hydrophilic layer.

The layer can be embodied all-over the side of the base plate and/or of the cover plate facing away from the receiving area, in particular such that an immersion oil, in particular in case of oil immersion microscopy, does not wet the layer. The layer can be embodied all-over the side of the base plate and/or of the cover plate facing the receiving area, in particular with the exception of the receiving area.

It is, for example, an advantage if areas of the base plate and/or of the cover plate to be glued are hydrophilized.

In the sample chambers described above, in a predetermined surface area, a double layer of a hydrophilic and an oleophobic layer can be provided. This means that one of the two layers is provided on the other one. Here, in particular the layer directly applied to the plastics, in particular the base plate or the cover plate, can comprise a larger area than the other layer of the double layer. With such a double layer, resistance with respect to or repellence of various liquids can be simultaneously enabled.

In the sample chambers, a plurality of layers which are in particular spatially separated can be provided. Thereby, at predetermined areas, suited resistance or suited repellence can be purposefully achieved. In particular, for example in an area at the outer surface of the sample chamber, a first surface area with a first layer can be provided, and in a receiving area, which is, for example, formed by a hollow space, a further surface area with a second layer can be provided.

The invention furthermore provides a sample chamber of plastics with at least one receiving area for receiving a liquid, wherein the sample chamber comprises a lattice. By a lattice or grid, for example different observation or examination fields can be defined.

The sample chamber can in particular comprise the above-described elements (for example a base plate and/or a cover plate as described above) and/or properties.

The web thickness (or web width) of the lattice can be between 1 μm and 1 mm, in particular between 10 μm and 100 μm. The recurrent distance (lattice constant) between the webs can be between 10 μm and 2 mm, in particular between 50 μm and 1000 μm. The lattice can be in particular a rectangular lattice, for example a square lattice.

The lattice can be arranged in particular in the area of a receiving means. The lattice can be arranged to be rigid or immovable. The sample chamber can comprise a plastic body; then, the lattice can be embodied as part of the plastic body, incorporated in the plastic body, and/or be all-over connected with the plastic body. If the lattice is embodied as part of the plastic body, this means that no additional material is required for the lattice and that it is instead obtained by processing the plastic body.

In particular, the lattice can be an embossed lattice. In this manner, a simple manufacture is possible and the resulting lattice is arranged in a fixed position.

The sample chamber can be in particular one of the sample chambers described above. The sample chamber can comprise a base plate and/or a cover plate and the lattice can be arranged at the base plate or the cover plate, in particular embossed into the base plate or the cover plate.

The lattice can be applied by embossing, in particular by hot embossing, lasing or imprinting.

The invention furthermore provides a method of manufacturing a sample chamber with a plastic body with the following steps:

providing a plastic body,
attaching a lattice at the plastic body.

The sample chamber can in particular be one of the sample chambers described above. The plastic body can then be the base plate or the cover plate.

The attaching step can be performed by means of embossing, in particular by means of hot embossing, imprinting or lasing. The step of embossing can be performed with an embossing die, in particular a heated embossing die. The embossing die thus forms an embossing master which represents a negative of the shape to be embossed. The embossing die can comprise steel, nickel or silicon.

Basically, the embossing die can have a temperature of room temperature to 250° C. In particular, the temperature of the embossing die can be between 20° C. below and 20° C. above the glass transition temperature of the plastic body. In particular, the temperature of the embossing die can be 5° C. to 15° C. above the glass transition temperature. Embossing can be performed with a force of 100 mN to 5 kN, in particular 100 N to 2 kN. The time of embossing can be between 10 ms and 1 min, in particular 300 ms and 5 s. The time of embossing can be in particular selected in response to the temperature of the embossing die and the embossing pressure.

Before the attachment step, solubilization of the plastic body can be performed by means of a liquid which is a swelling agent for the plastics. With this, the plastic body is (at least superficially) swelled. For example, a surface area of the plastic body to be embossed can be vetted with the liquid for this.

Alternatively, the solubilization can comprise the following steps:
providing the liquid at room temperature,
arranging the plastic body at a predetermined distance above the liquid surface, wherein a surface of the plastics is exposed to the liquid steam for a predetermined period.

The swelling agent thus does not have to be heated to an increased temperature but can be provided at room temperature. Thus, the temperature of the liquid steam also is at room temperature. The plastic body and/or the embossing die, too, can have room temperature. In particular the embossing die can also have a temperature above room temperature. Possible swelling agents to be used in the method are, for example, chloroform, acetone, toluene, benzene, heptane, ethanol, styrene, or mixtures thereof.

The predetermined distance can be in a range of approximately 0.1 to 10 cm, preferably approximately 0.5 to 5 cm, most preferred approximately 1 to 2 cm, and/or the predetermined period can be in the range of 0.2 to 300 s, preferably approximately 0.5 to 200 s, most preferred 1 to 10 s.

The sample chamber can comprise a base and a cover plate of plastics and the step of attaching can be performed at the cover plate. In this manner, the lattice is arranged at the cover plate before the base plate is connected with the cover plate, in particular in the area of the receiving area for receiving a liquid.

The method can furthermore comprise a connection of the cover plate with a base plate. The connection can be achieved by means of adhesives, solvents, UV treatment, radioactive treatment, laser treatment or thermal bonding. The bonding can be, in particular, ultrasonic bonding. Thermal bonding can be effected sheet-like or strip-like, in particular only along the edge of the base plate and/or the cover plate.

In particular if attaching includes a solubilization of the cover plate, connecting can comprise pressing together the solubilized surface of the cover plate and a surface of the base plate, in particular at room temperature, so that the base plate and the cover plate are connected to each other. The solubilization of the surface thus serves the double purpose of attaching the lattice in a facilitated manner and of connecting the base plate with the cover plate. For this, the step of pressing together can be performed in particular directly after the step of attaching the lattice. An additional treatment step for connecting the two plates is then not necessary.

Further features and advantages will be described below with reference to the exemplary figures. In the drawings:

DETAILED DESCRIPTION OF THE INVENTION

Figure 1:
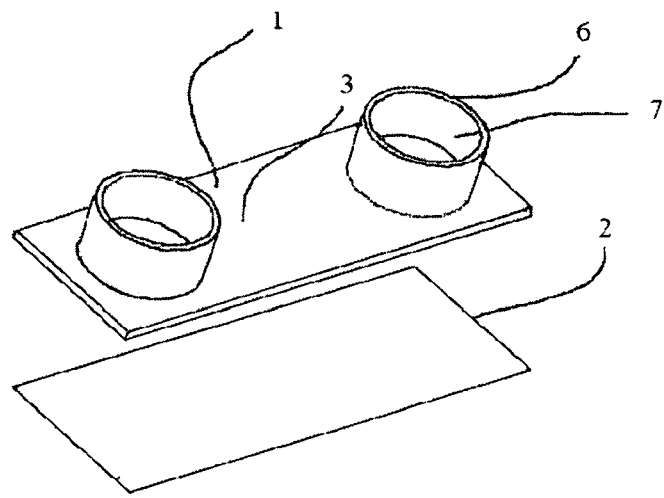
FIG. 1 shows an exploded view of an example of a sample chamber.
Figure 2:
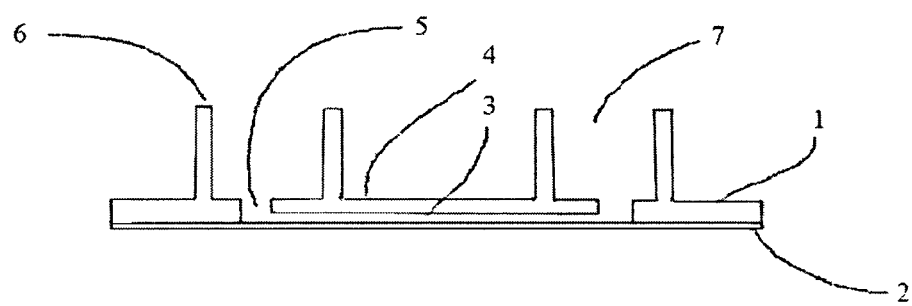
FIG. 2 shows a cross-sectional view of an example of a sample chamber.

FIG. 1 schematically illustrates an example of a sample chamber comprising a base plate 1 and a cover plate 2. In the base plate 1, an oblong depression 3 is provided. As can be seen in particular in FIG. 2, which shows a cross-sectional view corresponding to FIG. 1, the depression 3 comprises a base, that means it is embodied in the form of a groove, so that in this manner, by the combination of cover plate 2 and base plate 1, a receiving means or a reservoir is formed in the form of a hollow space or a channel in the sample chamber.

At the ends of the oblong depression, a through hole 5 each is embodied in the base plate. The channels formed in this manner serve as inflow or outflow for the receiving area formed by the depression 3. In this manner, a flow chamber is formed.

The surface of the base plate 1 opposite the depression 3 has a planar design over a large surface area. However, it comprises two elevations 6 in each of which a recess 7 is embodied. In this manner, two further receiving areas for liquids (reservoirs) are provided which are each fluidically connected with the reservoir formed by the depression 3 by means of a through hole 5.

The base plate and the cover plate consist of plastics, in particular of the same plastics. The base plate can in particular be a molded body. In the manufacture of the sample chamber, in particular by means of injection molding and subsequent connecting of the base plate with the cover plate, for example by gluing or bonding, tensions can form in the plastics. If furthermore adhesives or solvents are used, the joints can become an access for a creeping agent. If corresponding solvents or creeping agents, for example oils, are used, these can penetrate the sample chamber and lead to tension cracks.

Such a penetration of creeping agents or solvents can be prevented by an appropriate coating of the sample chamber. Here, in particular a hydrophilic layer is advantageous.

If the cover plate and the base plate are connected to each other by means of thermal bonding or gluing, the base plate and the cover plate can be, for example, all-over provided with a hydrophilic layer on one or several sides. Depending on the type of examinations to be performed in the receiving area 3, this receiving area can, however, be excluded from the layer.

Such a hydrophilic layer can, for example, be achieved by means of plasma technologies where $SiO_x$ is deposited. $SiO_x$ has a surface tension of above 72 mN/m. Mainly predetermined areas, for example the receiving area, can be excluded from coating. For this, corresponding shadow masks are used during coating.

Possible methods for such layers can be taken, for example, from B. Jacoby et al., "Abscheidung Charakterisierung und Anwendung von Plasma-Polymerschichten auf HMDSO-Basis", Vakuum in Forschung und Praxis (2006), pages 12-18, or D. Hegemann et al., "Deposition Rate and Three-dimensional Uniformity of RF plasma deposited $SiO_x$ films", Surface and Coating Technology (2001), page 849.

If the base plate and the cover plate are connected to each other by solubilizing the plastic surface of at least one of the two plates and subsequent pressing together, the surfaces to be connected to each other are advantageously not coated with a hydrophilic layer. In this case, for example the respective surfaces of the base and cover plate, respectively, facing away from the other plate are coated with a hydrophilic layer. Thus, in the finished sample chamber, the surfaces facing outwards are coated.

As an alternative or in addition to a hydrophilic layer, an oil-repelling layer can be provided. Such an oleophobic layer can be applied, for example, spatially separated from a hydrophilic layer or else onto a hydrophilic layer. Such oleophobic layers are in particular advantageous when oil immersion objectives are used, in that the sample chamber can be easily cleaned. Such oil immersion objectives are in particular used in high-resolution microscopy where then immersion oil wets the sample chamber. In particular in inverse microscopy, the complete bottom of conventional sample chambers is then wetted with oil. Apart from the bad cleaning possibilities, such a wetting has the further disadvantage that during screening (moving along the sample chamber), the oil amount is decreasing as the oil adheres to the plate and thus an insufficient amount of oil remains between the objective lens and the sample chamber bottom.

To avoid these disadvantages in connection with immersion objectives, the oleophobic layer advantageously has a lower surface tension than that of the immersion medium (oil or water). Creeping of an oil into the plastics of the sample chamber can also be prevented by an oleophobic or also by a hydrophilic layer. With this, it is prevented that tension cracks occur or residual material present in the plastics (catalysts, UV accelerators, softening agents, etc.) are separated off. For this purpose, in particular an oil-repellent layer with a surface tension of less than 20 mN/m, in particular less than 15 mN/m is particularly advantageous.

If embryos are cultivated, these are always cultivated in medium drops having a size of up to 5 mm (aqueous solution). These drops are embedded in oil, and per sample chamber, 1 to 50 medium drops can be present. An oleophobic layer in the receiving area prevents oil from penetrating the plastics and releasing growth inhibiting substances. In the same manner, for this, a hydrophilic layer, for example of $SiO_x$, can be provided.

Figure 3:
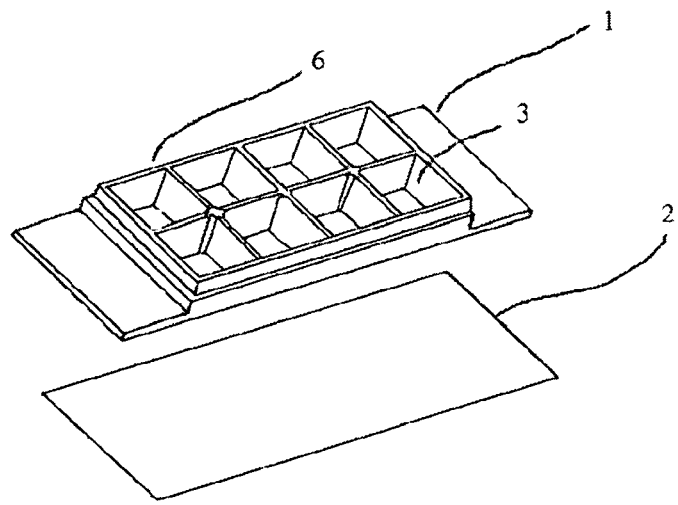
FIG. 3 shows an exploded view of another example of a sample chamber.

In FIG. 3, an example of a further sample chamber is schematically illustrated. This sample chamber also comprises a base plate 1 and a cover plate 2. In the base plate 1, eight depressions 3 are provided. These depressions do not comprise any bottom and are thus embodied as through hole in the base plate. By corresponding elevations 6, eight receiving areas or reservoirs are formed which are completely open to the top or outside.

With such sample chambers, a layer on the walls (elevations, webs) separating the reservoirs can prevent cross-contamination between the reservoirs. Creeping of aqueous media is thus minimized. In many cell media, proteins are contained which can wet surfaces with surface tensions of more than 25 mN/m. Without an oleophobic layer, these proteins are absorbed, in conventional sample chambers, at the webs between adjacent reservoirs, so that a surface tension of more than 72 mN/m can result which then leads to cross-contamination. Such a protein adsorption, however, is reduced according to the invention by a lipophobic layer.

If the base plate 1 comprises an oleophobic or hydrophilic layer, the cover plate 2, however, does not comprise such a layer, this results in a surface tension difference between the bottom of the receiving areas (observation area) and the surface of the base plate. In this manner, a negative capillary action is generated by which a leakage of sample liquid from the receiving areas is prevented.

Basically, the coating of the sample chamber can be performed at different points in time. According to a first alternative, coating is performed in a sample chamber of a cover plate and a base plate before the two plates are connected.

According to a second alternative, the base plate and the cover plate can be connected to each other, and subsequently a coating treatment can be performed. For this, for example a plasma treatment with atmospheric plasma can be performed. Here, atmospheric plasma means plasma which is not ignited at an underpressure with respect to atmospheric pressure. It can be in particular a corona treatment with ambient air as active or process gas, or atmospheric plasma with nitrogen as active or process gas. In particular if nitrogen is used, a particularly distinct and durable hydrophilic layer can be achieved. To guide the plasma for example through hollow space structures in the sample chamber, an overpressure of the plasma gas is advantageous. Here, values of between 1 bar and 8 bar are particularly suited.

Another coating arrangement is to provide a receiving area with an oil-repellent layer, except for small surface areas which have a diameter of, for example, between 1 μm and 100 μm. The excluded areas can remain untreated or be, for example, hydrophilized. Thereby, cells can be cultivated on certain spots and a cell array can be generated. In such a case, a cell suspension can be introduced into the receiving area. The cells only adhere to those surface areas which have not been provided with an oleophobic coating. Then, the cell medium can be exchanged and for example replaced by an oil or a serum-free medium. A corresponding result can be achieved if the receiving area is all-over coated with an oleophobic layer, and subsequently a hydrophilic layer is applied to predetermined, spatially separated spots, so that in these areas, a double layer of an oleophobic and a hydrophilic layer is obtained.

Figure 4:
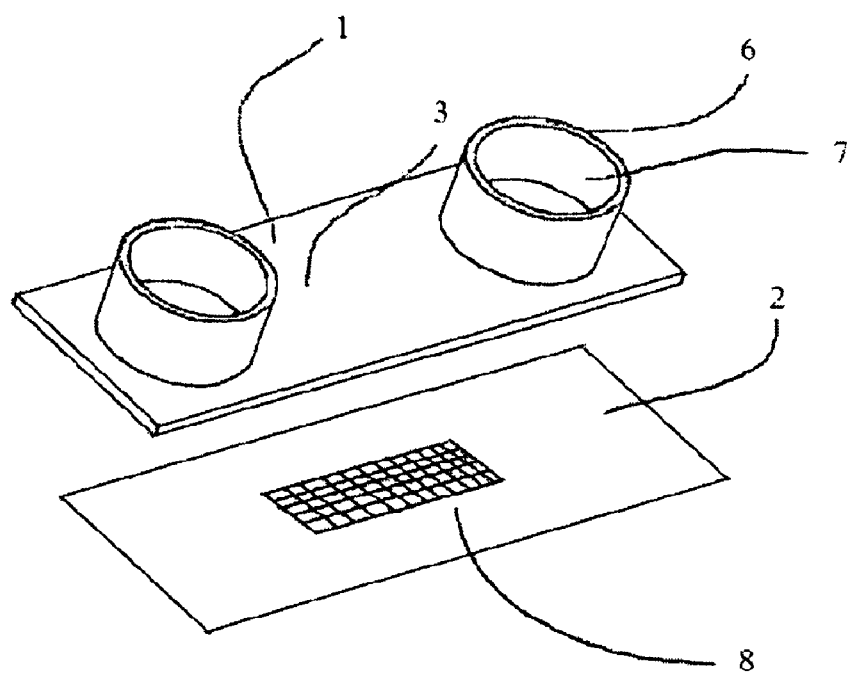
FIG. 4 shows an exploded view of an example of a sample chamber with a lattice.

FIG. 4 schematically illustrates a sample chamber in which in the area of the receiving area, a grid or lattice 8 is provided. The shown lattice is in particular a rectangular lattice. The other elements of the sample chamber can in particular correspond to those of FIG. 1.

The lattice 8 can be principally applied by embossing, in particular by hot embossing, lasing or imprinting. If imprinting is employed, in particular screen printing can be used.

Alternatively, the lattice 8 is incorporated into the cover plate 2 by embossing, for which a corresponding embossing die is used.

For this purpose, in particular the cover plate 2, which is embodied, for example, in the form of a film, can be swelled with a solvent (such as chloroform, acetone, toluene or benzene, or mixtures thereof). For this, the film can be in particular exposed to a swelling agent steam. Then, the lattice can be embossed into the plastics of the film 2 at room temperature. Instead of the film, the swelling agent and the embossing die having room temperature, it is also possible for one or several of these elements to have an increased temperature compared to room temperature. For example, the embossing die can be heated.

Directly after the embossing of the lattice, the cover plate with its still solubilized surface can be connected with the base plate by pressing them together. This step, too, can be performed, in particular, at room temperature. Thus, by the solvent, on the one hand the embossing of the lattice is facilitated, and on the other hand the bonding by means of a solvent is permitted. For the connection, furthermore the surface of the base plate facing away from the cover plate can be swelled. It is furthermore an advantage if both plates consist of the same plastics.

It should be clear that the above-described features can also be combined with each other in another way. Furthermore, in particular the illustrated coating possibilities and arrangements can also be employed e.g. for sample chambers which only consist of a plastic body, for example of a molded body, and which do not have to be produced by connecting a base plate with a cover plate. With such sample chambers, for example the receiving area (reservoir) is formed by a depression with base and/or elevations.

The invention claimed is:

1. Sample chamber of plastics with at least two receiving areas for receiving a liquid, wherein the sample chamber comprises an oleophobic layer in a predetermined surface area between the at least two receiving areas,
wherein the sample chamber comprises a base plate and a cover plate firmly connected thereto and wherein the oleophobic layer is disposed on at least one of a side of the base plate facing away from the receiving areas, and a side of the cover plate facing away from the receiving areas.

2. Sample chamber according to claim 1, wherein the oleophobic layer has a surface tension of less than 25 mN/m.

3. Sample chamber according to claim 1, wherein the oleophobic layer has a layer thickness of 1 nm to 50 μm.

4. Sample chamber according to claim 1, wherein the oleophobic layer has an area of 1 μm$^2$ to 10 cm$^2$.

5. Sample chamber according to claim 1, wherein the base plate comprises at least one of
at least one depression, and
at least one elevation,
by which a receiving area is formed.

6. Sample chamber according to claim 1, wherein a depression is provided in the base plate, so that a receiving area is formed by the base plate and the cover plate.

7. Sample chamber according to claim 6, wherein the depression in the base plate comprises a base, so that a hollow space is formed by the cover plate.

8. Sample chamber according to claim 1, wherein the cover plate has a thickness of 50-250 μm.

9. Sample chamber according to claim 1, further comprising an additional predetermined surface area, including at least one of a hydrophilic layer and a second oleophobic layer.

10. Sample chamber of plastics with at least one receiving area for receiving a liquid, wherein the sample chamber comprises an oleophobic layer in a predetermined surface area,
wherein the sample chamber comprises a base plate and a cover plate firmly connected thereto and wherein the oleophobic layer is disposed all-over at least one of a side of the base plate facing away from the receiving area, and a side of the cover plate facing away from the receiving area.

11. Sample chamber according to claim 10, wherein the oleophobic layer has a surface tension of less than 25 mN/m.

12. Sample chamber according to claim 10, wherein the oleophobic layer has a layer thickness of 1 nm to 50 μm.

13. Sample chamber according to claim 10, wherein the base plate comprises
at least one of
at least one depression, and
at least one elevation,
by which a receiving area is formed.

14. Sample chamber according to claim 10, wherein a depression is provided in the base plate, so that a receiving area is formed by the base plate and the cover plate.

15. Sample chamber according to claim 14, wherein the depression in the base plate comprises a base, so that a hollow space is formed by the cover plate.

16. Sample chamber according to claim 10, wherein at least one of the base plate and the cover plate comprises a channel coming from outside and ending in the receiving area.

17. Sample chamber according to claim 10, wherein the cover plate has a thickness of 50-250 μm.

18. Sample chamber according to claim 10, wherein a double layer of a hydrophilic layer and an oleophobic layer is provided in the predetermined surface area.

19. Sample chamber according to claim 10, wherein a plurality of oleophobic layers which are spatially separated is provided.

20. Sample chamber according to claim 10, further comprising a lattice.

21. Sample chamber according to claim 20, wherein the lattice is arranged in the area of a receiving means.

22. Sample chamber according to claim 20, wherein the lattice is an embossed lattice.

23. Sample chamber according to claim 22, wherein the sample chamber comprises at least one of a base plate and a cover plate, and the lattice is embossed into the at least one of the base plate and the cover plate.

24. Sample chamber according to claim 20, wherein the lattice is applied by embossing according to a process selected from the group consisting of hot embossing, lasing, and imprinting.

25. Sample chamber according to claim 10, further comprising an additional predetermined surface area, including at least one of a hydrophilic layer and a second oleophobic layer.

26. Sample chamber according to claim 25, wherein the additional predetermined surface area is arranged in the at least one receiving area.

27. Sample chamber according to claim 25, wherein the at least one of a hydrophilic layer and a second oleophobic layer is disposed on at least one of the side of the base plate facing the at least one receiving area and the side of the cover plate facing the at least one receiving area, and is disposed across the entire surface of the at least one of the side of the base plate facing the at least one receiving area and the side of the cover plate facing the at least one receiving area, except for the receiving area.

* * * * *